United States Patent [19]

Siegmund

[11] 4,025,965
[45] May 31, 1977

[54] INTRAOCULAR LENSES

[75] Inventor: Walter P. Siegmund, Woodstock, Conn.

[73] Assignee: American Optical Corporation, Southbridge, Mass.

[22] Filed: Mar. 16, 1976

[21] Appl. No.: 667,318

[52] U.S. Cl. .................................................. 3/13
[51] Int. Cl.² ....................... A61F 1/16; A61F 1/24
[58] Field of Search ....................................... 3/13, 1

[56] References Cited

UNITED STATES PATENTS

| | | |
|---|---|---|
| 2,834,023 | 5/1958 | Lieb ............................................. 3/1 |
| 3,673,616 | 7/1972 | Fedorov et al. ........................... 3/13 |
| 3,906,551 | 9/1975 | Otter ............................................ 3/13 |

FOREIGN PATENTS OR APPLICATIONS

| | | | |
|---|---|---|---|
| 959,314 | 3/1957 | Germany .................................. 3/13 |

OTHER PUBLICATIONS

"New Lens for Cataracts" Newsweek, June 30, 1975, p. 45.

Primary Examiner—Ronald L. Frinks
Attorney, Agent, or Firm—H. R. Berkenstock, Jr.; William C. Nealon

[57] ABSTRACT

Optical sections (lenses) of pseudophakoi having tangential holes are produced without drilling operations. A preform of lens material is drawn with embedded acid soluble rods and/or openings corresponding in diametral size and relative juxtaposition to the size, shape and locations of holes needed in a lens, a lens blank is cut from the drawn preform and portions of rods remaining therein are etched away prior to or following final edging and surface finishing of the lens blank.

7 Claims, 10 Drawing Figures

INTRAOCULAR LENSES

BACKGROUND OF THE INVENTION

1. Field of the Invention

This invention relates to improvements in artificial intraocular lenses (pseudophakoi) and has particular reference to the manufacture of perforate optical sections (lenses) of pseudophakoi to which haptic sections (iris clips) may be fitted.

2. Discussion of the Prior Art

Well-fixed and well-centered intraocular lens implants are known to produce stable retinal images and offer the best chance of re-establishment of binocularity in cases of aphakia.

Many techniques of lens implantation, including suturing to the ciliary muscle as disclosed in U.S. Pat. No. 3,711,870 and iris diaphragm fixation as discussed in U.S. Pat. No. 3,673,616 for example, have been used. The latter is considered to be a safe procedure giving good stability and the present invention deals more particularly with improvements in this general type of pseudophakos but also has applicability to the former and/or any other type of pseudophakos requiring the provision of holes in its lens through which sutures may be extended or within which iris clips or other fastening wires may be inserted and anchored.

In cases of iris diaphragm fixation, "iridocapsular" and/or "iris clip" pseudophakoi are used. These implants are provided with a fastening section comprised of posterior and/or anterior iris clips usually in the form of loops or struts of wire or wire-like material, the ends of which are anchored in holes provided in the lens of the pseudophakos.

In view of a requirement for carefully controlled exceptionally close tolerances of hole size of the minuteness required of such holes, e.g. from 0.1 to 0.2 mm for lenses having a full diameter of only approximately 4 mm, the practice heretofore of forming such holes with drills has presented serious problems of tediousness, high scrap yield and excessive product cost, not to mention other adversities such as roughness or incipient cracking of lens material within the holes and/or chipping or flaking adjacent or at opposite ends of the holes, all of which tend to weaken the lens structure and render it subject to damage when wire iris clips and the like are anchored therein.

It has also been a practice heretofore to extend iris clip anchoring holes in directions parallel to a lens axis and completely through the lens with the disadvantage of interrupting the otherwise smooth contour of the anterior surface of the lens. Holes extending through the front surface of a lens can interfere with lens insertion, trap tissue or fluids or otherwise be adverse to the acceptance and/or function of a pseudophakos.

A principal object of the present invention is to provide pseudophakoi of improved construction and more particularly to provide a novel lens structure and method for manufacturing perforated lenses of pseudophakoi; another object is to provide for the manufacture of tangentially perforated artificial intraocular lenses in an unusually simple, rapid and economical manner wherewith manufacturing output can be readily maximized at minimum product cost with improved product quality and dependability of duplication in mass production; and still another object is to provide a lens of unique peripheral configuration and having smooth uninterrupted anterior and posterior surfaces.

SUMMARY OF THE INVENTION

The aforesaid objectives and their corollaries are accomplished by drawing a lens-forming material in which is embedded acid soluble rods corresponding in diametral size and relative juxtaposition to the size and spaced parallel locations of holes needed in a lens. The drawing of a preform from which a multiplicity of lenses may be formed is contemplated.

The preforms may be constructed of two flat slabs of lens material each similarly semi-circularly or otherwise grooved along one side and interfacially assembled with corresponding grooves juxtapositioned to form openings through the assembly. Rods of selectively leachable material are placed in the openings and the assembly is drawn, as a unit, in the direction of the openings, into a bar of such reduced cross-sectional size that the openings and/or rods therewithin become spaced apart a distance equal to that desired of holes in a finished lens. The preform may be used without the rods of leachable material whereupon the drawn bar will have longitudinal holes extending therethrough in positions corresponding to those provided in the preform.

In either case, sides of the drawn bar which are parallel to the plane of the two holes are used as opposite faces of lens blanks to be formed therefrom. A blank is cut to desired peripheral configuration from the bar and ground and polished to final shape, thickness and edge configuration.

When leachable rods are included in the preform, their removal from the lens blank, before or after grinding and polishing of the lens blank, may be accomplished by immersion of the blank in an etching solution to which all parts of the blank, but the rods, are resistant.

Holes produced by drawing the preform without the inclusion of leachable rods obviates the necessity for leaching. Holes formed by this technique or that of using the leachable rods are, when finally formed, internally smoothly surface textured and free of incipient cracking, chipping, flaking or other roughnesses which are common to holes produced by prior art drilling operations.

Details of the invention will become more readily apparent from the following description when taken in conjunction with the accompanying drawings.

IN THE DRAWINGS

DESCRIPTION OF THE PREFERRED EMBODIMENTS

Figure 1:
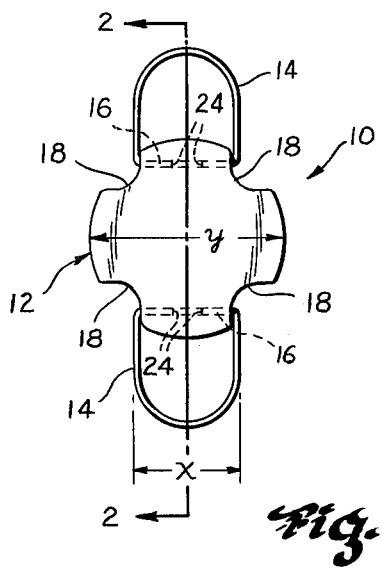
FIG. 1 is a front elevational view of an embodiment of the invention.
Figure 2:
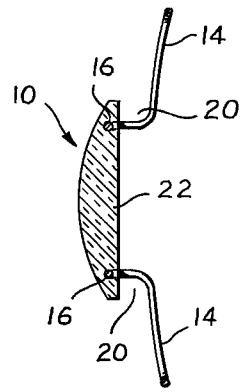
FIG. 2 is a cross-sectional view of the pseudophakos of FIG. 1 taken generally along line 2—2.

Referring more particularly to FIGS. 1 and 2 of the drawings, pseudophakos 10 comprises a lens 12 having a pair of posterior iris clips 14 for fixturing the pseudophakos within the eye of an aphakic. This general form of pseudophakos, i.e. having dual rearwardly and laterally extended iris clips 14, is commonly referred to as an "iridocapsular lens" or "two-loop lens". It is used after extracapsular cataract extraction and fixation is accomplished by placing the iris between the posterior surface of the lens and clips 14 thereby locating the clips in the iridocapsular cleft wherein they are ultimately held in place by posterior synechiae.

Lens 12 is formed of a material which is biologically inert, i.e. not susceptible to being absorbed by body fluids and capable of being well tolerated when implanted. Glass is a good example of such a material. Exemplary base glasses are soda borosilicates and sodium titania silicates wherein all raw materials, particularly $SiO_2$ are selected to be types which are free of traces of radioactive substances. Desirable glass compositions are those which may be produced according to standard glass-making techniques with raw materials consisting of high purity silica, nitrates of sodium and barium, carbonates of sodium, strontium, calcium and manganese and oxides of titanium, zirconium, cerium, boron, zinc, iron and copper. It is required, however, for the sake of maintaining high purity that such glasses be made in glass makers platinum crucibles and with similarly non-contaminating stirrers. It is also highly desirable that the lens material have optical transmission properties simulating the optical absorption of the human crystalline lens and exemplary glass compositions of this type are set forth in a copending application for patent, Ser. No. 615,276, which was filed on Sept. 22, 1975. Other ophthalmic lens glasses which are free from toxicity and radioactivity and are preferably of low density may, of course, be used. Other ophthalmic lens materials may include quartz, or methylmethacrylate resins such as those available under the tradenames "Lucite" and "Plexiglass" and biologically neutral, chemically pure polymethylmethacrylates or biologically inert polymeric materials.

Iris clips 14 which comprise loops of wire having their opposite ends secured to lens 12 are, for reasons of avoiding irritation and/or human body rejections, preferably formed of a biologically inert material such as platinum, titanium, tantalum or an extruded polyamide such as nylon or one or more of other resins including methylmethacrylate or biologically neutral chemically pure polymethylmethacrylates or biologically inert polymeric materials.

Iris clips 14 and others to be described hereinafter will be referred to as being "wire" or "formed of wire". Accordingly, it should be understood that the term "wire" as used in this specification and its appended claims is intended to include strands, strips, rods, filaments or fibers of biologically inert material whether the material is metallic or plastic and whether one or both is used to make up a particular array of iris clips or other lens-fastening components.

Iris clips such as 14 are conventionally fastened to lenses such as lens 10 by being force-fitted or otherwise entered into holes provided in the lenses. To this end, lens 10 is provided with tangential holes 16 of predetermined carefully controlled diametral dimension and relative juxtaposition, i.e. spacing, according to the locations desired for anchoring opposite ends of iris clips 14.

Lens 12 is notched or recessed adjacent each of opposite ends of holes 16 to provide the lens with an overall configuration of a cross which is illustrated in FIG. 1. These notches 18 make it possible to use relatively narrow clips 14, i.e. wherein the dimension $x$ thereof (FIG. 1) is substantially less than the overall diametral dimension $y$ of lens 12. Clips 14 are preferably arranged as illustrated in FIG. 12 so as to extend from opposite ends of openings 16 generally rearwardly and thence laterally so as to provide spacings 20 between the lens posterior surface 22 and their lateral extensions into which an iris diaphragm of an aphakic eye may be positioned as discussed hereinabove.

As can be seen from FIGS. 1 and 2, iris clips 14 are of the general configuration of a "bail" and may be attached to lens 12 in various ways. One form of attachment may be to simply pre-form the clips 14 to the configurations illustrated in FIGS. 1 and 2 and slip opposite ends 24 thereof into holes 16 by "springing" these ends apart and allowing the clips to resume their relaxed initial shape with ends 24 in place. This, of course, requires the materials to be characteristically capable of returning to an initial set after deformation. Titanium or stainless steel wire is exemplary of suitable materials.

Figure 5:
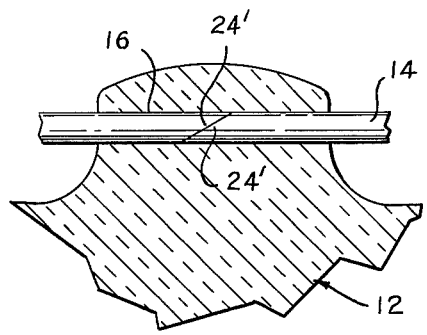
FIG. 5 is an enlarged fragmentary cross-sectional view of a pseudophakos wherein details of a particular feature of the invention are illustrated.

Should it be necessary or desirable to use a relatively soft wire such as gold, platinum or a plastic material, fusion of the opposite ends of a clip inside holes 16 may be accomplished. For example, by scarfing the opposite ends of a clip 14, as has been illustrated in enlarged detail in FIG. 5, these ends 24' may be made to overlap. Fusion of ends 24' together and with clip 14 in place, may then be accomplished with a laser beam directed through the material of lens 12 and focused upon ends 24'. Alternatively, ends 24' may be heated by inducing an electrical current in the wire of clip 14 with a strong magnetic field whereby the added contact resistance at the junction of ends 24' can cause heating and fusion. It should be understood, however, that ends 24 of clips 14 may be force-fitted into holes 16 by careful control of the relative diametral sizes of holes 16 and the wires which make up clips 14. The former assembly techniques which avoid interference fitting also avoid possibilities of adverse stressing of the lens materials adjacent holes 16.

Figure 3:
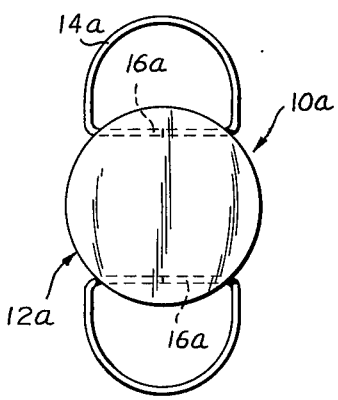
FIG. 3 is a front elevational view of a modification of the invention.
Figure 4:
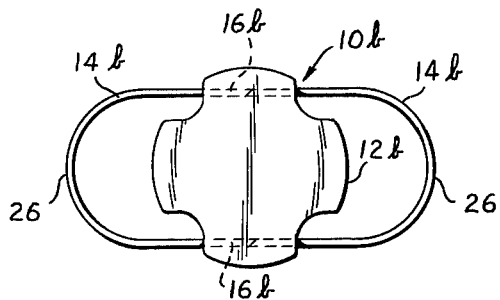
FIG. 4 is a front elevational view of still another modification of the invention.

Illustrated in FIGS. 3 and 4 are other configurations of pseudophakoi having similarly continuous, i.e. uninterrupted, front and rear surfaces resulting from the use of tangential holes.

In FIGS. 3, for example, pseudophakos 10a comprises lens 12a having a completely circular peripheral configuration, i.e. notches 18 of FIG. 1 are not used. Iris clips 14a of a generally wider dimension than clips 14, but otherwise similar in shape and placement, extend outwardly and generally rearwardly of opposite ends of holes 16a. The fastening of clips 14a to lens 12a would be accomplished as described hereinabove relative to matters of clips 14 of FIG. 1.

In the modification of the invention illustrated in FIG. 4, pseudophakos 10b comprises lens 12b having a similar configuration to that of lens 12 of FIG. 1. Opposite ends of iris clips 14b, however, are extended from holes 16b axially thereof to the points where loops 26 are formed. Immediately adjacent to opposite ends of hole 16b each of clips 14b are displaced somewhat rearwardly of the posterior surfaces of lens 12b.

In all embodiments of the invention illustrated in FIGS. 1-5 and discussed hereinabove, iris clips of the pseudophakoi are fastened in holes extending tangentially through their respective optical sections (lenses). Interruptions of the smoothness of optically finished front and back surfaces of the lenses is avoided and fastening of the clips as bails under spring tension may be accomplished to avoid the introduction of forces or stress in the lens materials. These parallel tangentially oriented holes have other advantages already described.

Figure 6:
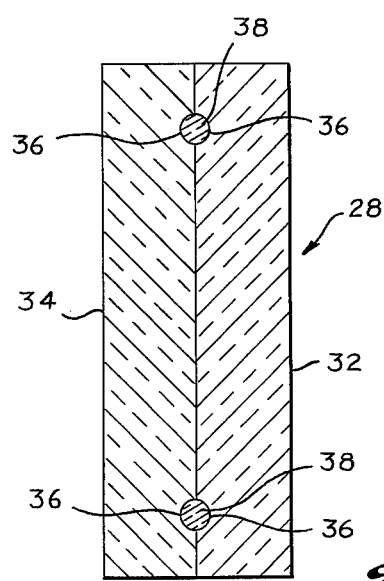
FIGS. 6–10 are illustrations of steps of a preferred method of making pseudophakoi according to the invention.
Figure 7:
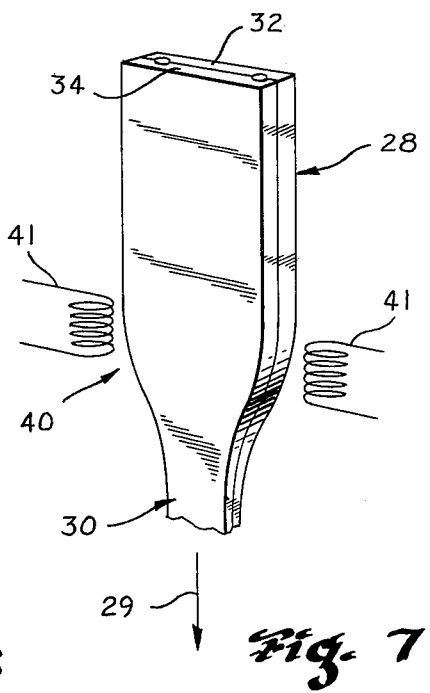

Lenses 12, 12a, 12b and/or variations thereof may be produced as follows:

Referring more particularly to FIGS. 6-10, a preform 28 (FIGS. 6 and 7) of bar 30 (FIGS. 7 and 8) from which individual lenses may be cut is prepared as follows:

A pair of slabs 32 and 34 of lens material, e.g. glass, are each provided with a pair of parallel semi-circular channels extending along one side. The channels in each slab 32 and 34 are spaced equal distances apart so as to communicate directly with each other when placed in face-to-face relationship by assembling slabs 32 and 34 as illustrated in FIG. 6. Adjoining channels 36 form circular openings through the assembly of slabs 32-34 into each of which a rod 38 of leachable material may be placed or, if desired, the circular openings may be left open.

Rods 38 may be formed of a glass which is selectively leachable in hydrochloric acid or other similarly leachable materials such as aluminum which can be drawn at most glass drawing temperatures and leached, e.g. with sodium hydroxide.

It should be understood that while the general configuration of preform 28 which has been illustrated in FIG. 6 may be preferred, other assemblages of differently shaped and/or numbers of pieces of lens materials and/or leachable filler materials replacing rods 38 may be used. It is only necessary to provide an assemblage of parts which, when heated and fused together, will produce the configuration of a main body of lens material having a pair of parallel channels extending longitudinally therethrough internally of the main body.

Those interested in details of glasses useful for slabs 32 and 34 may refer to the above-mentioned application for patent Ser. No. 615,276. Compatible leachable glasses and other materials of which rods 38 may be fabricated are set forth in U.S. Pat. Nos. 3,004,368; 3,624,816 and 3,899,314.

Having assembled the parts of preform 28, they are held firmly together, e.g. with clamps and/or heating and light fusion, and the preform is extended longitudinally into a heating zone 40 (FIG. 7) to be drawn longitudinally into bar 30. Electrical heating elements 41 which may be in the form of coils or rings and/or gas flames or other suitable heating means may be used to produce the heat in zone 40.

As bar 30 is drawn by baiting and pulling preform 28 in the direction of arrow 29, the main body of preform 28 is progressively lowered into zone 40 at a rate sufficient to permit a continuous formation of bar 30.

It should be understood that while the aforesaid operation may be performed with heat of a temperature sufficient to permit the drawing of preform 28 in zone 40, e.g. 550° to 700° C, the preform may, alternatively, be shaped into the configuration of bar 30 by pressure rolling at a lower temperature but one which is sufficient to fuse all lens-forming glass components together into a unitary structure.

Having formed bar 30, it is cut or broken away from remaining portions of preform 28. Lens blanks 42 are then sawed, ground ultrasonically, trepanned or otherwise cut from bar 30 as illustrated in FIG. 8, for example.

Figure 8:
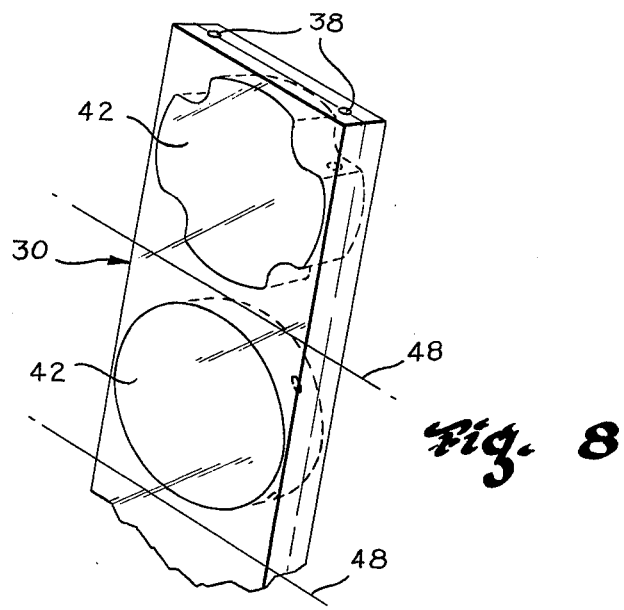

In the uppermost portion of FIG. 8, there is illustrated a lens blank 42 having the general configuration of lens 12. Therebeneath and for purposes of illustration only is shown another lens blank 42 having the completely circular peripheral configuration of lens 12a described hereinabove. Once removed from bar 30, the lowermost circular lens blank 42 may be additionally ground or cut so as to form the notches 18 of lens 12 which are shown in FIG. 1.

Figure 9:
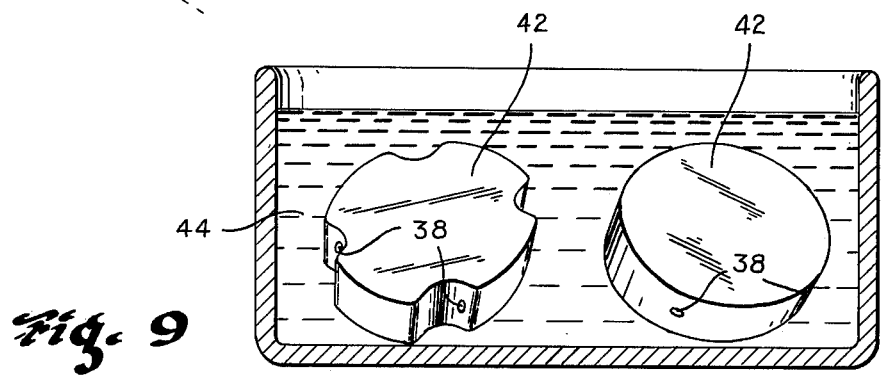

In the case of either of lens blanks 42, they are preferably immersed in a medium 44 such as hydrochloric acid, e.g. as illustrated in FIG. 9, to remove remaining portions of the drawn rods 38. Should, however, preform 28 not contain leachable rods 38, the operation of FIG. 9 is omitted.

Figure 10:
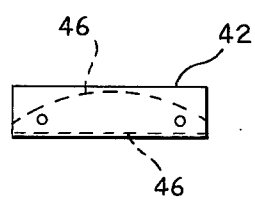

Finally, lens blanks 42 are ground, polished and edge finished to the final configuration and surface texture desired. FIG. 10 illustrates, with dot-dash outline 46, a surface shape which may be imparted to a blank 42 for completing a lens. The leaching operation depicted in FIG. 9 may be delayed until final grinding and/or polishing of the lens has been completed, if desired.

It is also contemplated that bar 30 may be initially cut into rectangular sections, e.g. by straight cuts along dot-dash lines 48 prior to the shaping of lens blanks 42 and the resulting rectangular segments of bar 30 may be placed in a suitable leaching solution to remove drawn rods 38 before shaping into blanks 42.

The artisan will readily appreciate that there are various other modifications and adaptations of the precise forms of the invention herein shown which may be made to suit particular requirements. Accordingly, the precise forms of the invention herein shown and described are not to be interpreted as restrictive of the invention beyond that necessitated by the following claims.

I claim:

1. A pseudophakos comprising a lens having uninterrupted smoothly optically finished opposite anterior and posterior sides and a pair of open-ended tangentially directed holes, one extending parallel to the other adjacent opposite sides of said lens, an iris clip of wire having opposite ends extended into and fixed against accidental withdrawal from each of said holes, said clip being in the form of a loop extending from said holes rearwardly away from said posterior surface of said lens a substantial distance and thence generally laterally thereof whereby marginal portions of the iris diaphragm of an aphakic eye may be positioned between said posterior surface of said lens and said laterally directed looped portions of said clips for fixation of the pseudophakos in the eye.

2. A pseudophakos according to claim 1 wherein said lens is of generally circular peripheral configuration.

3. A pseudophakos according to claim 1 wherein said lens is provided with inwardly directed notches adjacent each of open ends of said tangentially directed holes and wherewith said lens is afforded the overall configuration of a cross.

4. A pseudophakos according to claim 1 wherein each of said iris clips is formed of a resilient shape-retaining material and said opposite ends thereof are fixed against accidental withdrawal from said holes under spring tension in said wires of said clips.

5. A pseudophakos according to claim 1 wherein said opposite ends of said iris clips are force-fitted into said holes in said lens for prevention of accidental withdrawal thereof.

6. A pseudophakos according to claim 1 wherein said opposite ends of each iris clip are juxtapositioned in a respective hole receiving the same and joined together therewithin.

7. An artificial intraocular lens having uninterrupted smoothly optically finished opposite anterior and posterior sides and a pair of open-ended tangentially directed holes one extending parallel to the other adjacent opposite sides of said lens, the edge of said lens being recessed inwardly adjacent each of opposite ends of each of said holes whereby said anterior and posterior surfaces are provided with corresponding generally cross-shaped configurations.

* * * * *